United States Patent [19]

Behjati et al.

[11] Patent Number: 5,169,698

[45] Date of Patent: Dec. 8, 1992

[54] COMPOSITE MATERIAL FOR USE IN MEDICINE

[75] Inventors: Baratollah Behjati, Henstedt-Ulzburg; Klaus J. Holstein, Hamburg; Harri Rings, Dusseldorf, all of Fed. Rep. of Germany

[73] Assignee: Johnson & Johnson Orthopaedics, Inc., Raynham, Mass.

[21] Appl. No.: 596,832

[22] Filed: Oct. 11, 1990

[51] Int. Cl.$^5$ ................................................ B32B 1/00
[52] U.S. Cl. ........................................ 428/68; 428/71; 428/74; 428/304.4; 428/317.1
[58] Field of Search ............... 428/304.4, 317.1, 317.3, 428/68, 71, 74

[56] References Cited

U.S. PATENT DOCUMENTS

| | | | |
|---|---|---|---|
| 2,697,434 | 12/1954 | Rodman | 128/90 |
| 3,649,436 | 3/1972 | Buese | 428/317.3 |
| 3,661,674 | 5/1972 | Higgs et al. | 428/304.4 |
| 4,748,974 | 6/1988 | Richter et al. | 128/91 R |
| 4,944,958 | 7/1990 | Langen et al. | 427/2 |

FOREIGN PATENT DOCUMENTS

3410169A1  9/1985  Fed. Rep. of Germany .

Primary Examiner—William J. Van Balen

[57] ABSTRACT

A composite material for making supporting dressings or supporting structures for medical use consists of a porous flexible carrier which is impregnated with an aqueous polymer dispersion, the polymer particles of which are capable of film formation on removal of water. This composite material can be stored in waterproof packaging, in the state ready for use.

5 Claims, No Drawings

COMPOSITE MATERIAL FOR USE IN MEDICINE

The invention relates to a composite material for making supporting dressings or supporting structures for medical use, based on a porous carrier which is coated or impregnated with a polymer material capable of film formation.

Supporting or reinforcing structures for use in various fields of medicine are in general in the form of bands, bandages and support materials or carrier materials. They are generally used for splinting bone fractures, for immobilizing injured joints and for support and immobilization in the case of ligament or muscle injuries. They can also be used for support in the case of muscular weakness or for correcting deformations.

For the medical field, for making supporting dressings for the treatment of fractures, fabric bands are known which contain polyurethanes or form polyurethane-ureas and which crosslink after the application as a result of moisture, such as are described, for example, in DE No. 2,353,212. To initiate polymerization and curing, previous immersion into water is necessary, which is frequently undesired by the user. Unduly high water temperatures here accelerate the polymerization reaction and, as a result, the quantity of energy released per unit time increases. This fact, and also putting on of too many plies, that is to say the so-called "oversizing" of such a dressing, can in certain circumstances lead to skin burns on the patient. It is felt to be a further disadvantage that working with such a supporting dressing requires gloves. Moreover, these bands must be manufactured with exclusion of moisture, in general in an environment having a relative humidity of less than 1%, and packaged in an air-tight and water-tight film of plastic/aluminum laminate or other completely tight packaging materials. Damaged or partially used packages are useless after a short time; only completely anhydrous fibers can be used as the carrier material. Toxicological problems due to free isocyanate can also not be completely excluded in manufacture and use.

Another dressing material, known from U.S. Pat. specification No. 3,683,903, for making supporting dressings consists of a layer of a porous flexible material which is impregnated with a solution of a thermoplastic resin in a volatile organic solvent. This dressing material can be stored in a closed container and is solidified, after the dressing has been applied, by evaporation of the volatile solvent.

For use as a supporting dressing in medicine, bands which can be reactivated are also known from U.S. Pat. specifications No. 2,218,710 and 3,649,319, wherein the gypsum normally used otherwise in supporting dressings has been replaced at least partially by polyvinyl acetate which, in the manufacture of the bands, is applied from an aqueous or alcoholic solution and then dried. Before use as a supporting dressing, these bands must be immersed into water or moistened in another way and thus have the undesired disadvantages, described above, of bands which can be activated.

The known dressing materials consisting of carrier materials and film-forming polymers must be reactivated before application either by heating or by impregnation with water and thus show the same disadvantages as the known gypsum dressings.

On the other hand, dressing materials, which are impregnated with a solution of a polymer in a volatile organic solvent, are admittedly ready for use immediately, but toxic solvent vapors arise when they are used and, furthermore, the organic solvents are harmful to the skin.

It is thus the object of the invention to provide a composite material which is suitable for making supporting dressings and supporting structures for medical use and which can be stored and handled without problems, is solvent-free and toxicologically acceptable, adapts easily to the limbs to be supported, and after curing, shows favorable properties, such as increased strength and light weight.

According to the invention, this object is achieved by means of a composite material for making supporting dressings or supporting structures for medical use, based on a porous flexible carrier which is coated or impregnated with polymer material capable of film formation, which is characterized in that the polymer material is in the form of an aqueous polymer dispersion, the polymer particles of which are capable of film formation on removal of water.

The composite material according to the invention contains a porous carrier which is in the solid state of aggregation. The term porous is here to be understood as the property of a body to contain pores of any desired shape, namely the interstices between the fibers in textiles and other fibrous materials or the pores in a foam material.

In foam materials or cured foams, the volumes not filled by the solid are described as pores, a distinction being made between open pores and closed pores. Open pores are generally understood as channels in a solid, starting at the surface of the latter, continuing into the interior thereof and, in some cases, penetrating right through it.

Frequently, the property of absorbency is coupled to the property of porosity via the capillary action of the pores. A material is described as absorbent which is capable of absorbing a quite considerable quantity of fluid in itself and retaining it at least partially.

Within the scope of the invention, those materials are preferred as carriers which, in addition to absorbency, also possess a certain flexibility, where flexible means that the material is at least approximately capable of adapting to given solid surfaces to is formable. Preferably, web-shaped, band-shaped or fibrous materials are used, such as flat textile structures, in particular nonwovens and woven textiles and knitted textiles, bands and cords.

For making the carrier material, natural or synthetic fibers are suitable. Suitable natural fibers can be of vegetable and/or animal origin. Vegetable fibers are understood both as vegetable fibers such as, for example, cotton and raffia fibers, for example flax, hemp and jute, as well as hard fibers, for example sisal. The animal fibers can be either wool, for example sheep's wool, or animal hair such as, for example, horsehair. Moreover, chemical fibers of processed and/or regenerated natural and/or synthetic polymers can be used as the carrier material. These include both modified natural substances such as, for example, viscose and cellulose acetate, and protein fibers as well as purely synthetic fibers, for example polyester fibers, polyamide fibers and PVC fibers.

Inorganic fibers, for example mineral fibers, rock fibers, glass fibers, carbon fibers, metal fibers and/or slag fibers, can also be used as the carrier material.

Furthermore, any combination of the abovementioned fiber types is possible as the carrier material, which can be in the form of a band, nonwoven, cord and/or flat textile structure in woven and/or nonwoven form.

Moreover, foam materials or sponges, above all of synthetic polymers, are particularly suitable as absorbent carriers. Such absorbent foam materials are known to a person skilled in the art, for example those based on polystyrene, polyvinyl chloride, polyethylene or polyurethane.

According to the invention, the carrier described above is at least partially impregnated with an aqueous polymer dispersion. The aqueous polymer dispersions, which can be used within the scope of the invention, often described synonymously as a (polymer) emulsion, are known to those skilled in the art and are widely used as adhesives. Examples of suitable polymer dispersions are described in Ullmann, Enzyklopydie der technischen Chemie [Encyclopedia of Industrial Chemistry], volume 14, pages 241 and 242.

Suitable polymer materials which are used according to the invention in the form of an aqueous dispersion for impregnating the carrier material, include homopolymers and/or copolymers of vinyl derivatives, such as vinyl esters, styrene, acrylic acid derivatives, methacrylic acid derivatives and organic polymers based on polyurethane, preferably polyurethane ionomers of the cationic and anionic type, in particular cationic ionomers based on polyurethane resins containing sulfonate groups and/or carboxyl groups.

Suitable polymers of vinyl derivatives are homopolymers and copolymers of vinyl esters, such as of vinyl acetate, vinyl propionate and higher vinyl esters, such as vinyl laurate and vinyl esters of fatty acids. These monomers can be used by themselves or in the form of a mixture. Suitable comonomers for vinyl acetate and vinyl propionate are especially maleic acid esters, acrylic acid esters, ethylene, vinyl chloride, unsaturated carboxylic acids as well as higher vinyl esters such as vinyl laurate and vinyl esters of fatty acids. Polyvinyl acetate is particularly preferred.

Polyvinyl acetate dispersions have been described, for example in U.S. Pat. specification No. 1,084,581.

Emulsion polymers or dispersion polymers are, at least in part, preferred as the polymer material. The preparation of such polymers is known to those skilled in the art as emulsion polymerization. The process principles are explained, inter alia, in Ullmann (loc. cit.), volume 19, pages 132 et seq., and in Encyclopedia of Polymer Science and Engineering, volume 6, Wiley & Sons, NY 1986,.pages 1–51. Methods based on this process and leading to polymer dispersions having novel, defined properties, have been described, for example, in DE Nos. 3,242,486 and DE 3,323,570.

The auxiliaries used for the emulsion polymerization are likewise known and can be divided essentially into initiators, emulsifiers and stabilizers or protective colloids. A wide range of these auxiliaries and a large number of different possible combinations are to be found in the literature.

The polymer dispersions used according to the invention as impregnating agents have a solids content of 30% by weight to 80% by weight. Aqueous impregnating agents having a solids content of less than 30% by weight are disadvantageous, since an unduly high proportion of water entails disadvantages in application, such as, for example, long curing and drying times or dripping of the impregnating agent out of the carrier due to an unduly. low viscosity. On the other hand, aqueous impregnating agents having a solids content greater than 80% by weight should not be used, in order to avoid, for example, a premature film formation during application. Preferred aqueous impregnating agents, which can be used within the scope of the invention, have a solids content from 50% by weight to 75% by weight.

The desired auxiliaries, contained in the composite material according to the invention, are known to those skilled in the art as auxiliaries for polymer dispersions, such as, for example, emulsifiers, anti-foams, fillers, plasticizers, tackifiers, thickeners, solvents, pH regulators, coloring pigments, preservatives, complexing agents, anti-aging and anti-fatigue agents and/or the like.

The impregnation of the carrier materials described with the likewise described impregnating agents can be carried out, for example, by immersing the carrier into the impregnating agent and subsequent dripping off after removal. Other types of application of the impregnating agent to the carrier are possible such as, for example, spreading, casting, spraying and blade-application. In the case of carriers in the form of bands, the impregnation can be effected, for example, by passing the band through a bath of impregnating agent and, if appropriate, subsequent squeezing by passing the impregnated band through the nip between two rollers running in opposite directions. If desired, such bands can subsequently be wound up into rolls. If appropriate, the solids content of the impregnating agent can be increased by suitable measures, known to those skilled in the art for water removal and/or by addition of redispersion powders, for example spray-dried synthetic resin dispersion, within the limits given according to the invention.

Because of the impregnating agents used according to the invention, the composite materials according to the invention do not yet show, in the state ready for use, any film formation and hence any tackiness. The film. formation starts only when the residual water contained in the impregnating agent is removed. Film formation is understood as the coalescence and/or fusion of polymer particles to form a film. The minimum temperature at which this takes place is called the film formation temperature. The polymer dispersions used according to the invention as impregnating agents are chosen such that the film formation temperature, preferably the white point, is below the application temperature. A person skilled in the art understands the white point to be the minimim film formation temperature, at which the dispersion just no longer drys up to give a homogeneous clear film. The composite materials according to the invention for adhesive purposes can be used under application conditions which allow a removal of water, for example by evaporation. The film formation can be initiated, or at least promoted, by heating, aerating and-/or addition of dehydrating agents.

In the state ready for use, the composite materials according to the invention can readily be stored over a prolonged period, if they have been packaged at least largely in a water vapor-tight manner. Even partly used- packages can readily be sealed again and stored at least for a limited time. Partial taking of the composite material in portions is thus possible. No special safety precautions are necessary in application. The application can take place in one working step, without preparatory measures and/or aftertreatment measures. However, measures known to a person skilled in the art, which promote evaporation or volatilization of the residual water, accelerate the film formation and shorten the drying time.

Those formulations can be chosen in which, after the drying process, the composite material no longer shows any tackiness, at least at room temperature and below, and thus represents a reinforced, preferably fiber-reinforced plastic, in which the carrier material is now embedded in a solid plastic matrix. The hardness, the strength, stiffness or flexibility of the composite can be adjusted to defined requirements by suitable choice of the carrier, the polymer dispersions used and the auxiliaries such as, for example, plasticizers. For such supporting composites, for example "hard" dispersions, such as, say, homopolymeric vinyl acetate, methacrylate or styrene dispersions, are selected. As a shortened list of examples of known plasticizers, plasticizers incorporated in the polymer, such as, for example, vinly laurate, polymeric plasticizers such as, for example, soft resins or polyesters of aliphatic carboxylic acids, and monomeric plasticizers such as, for example, phthalates may be mentioned.

By an appropriate selection of the dispersion or additives, the composite material can be adjusted such that it is either waterproof or re-emulsifiable after the drying process. For composite materials which are to be waterproof after drying, those synthetic resin dispersions can be used which allow crosslinking via the active groups, cf. Encyclopedia of Polymer Science and Engineering, J. Wiley & Sons, volume 8, pages 662 and 663, NY 1987, or via polydentate metal salts, as described in DE 3,434,668.

The composite material according to the invention can advantageously be stored, in the state ready for use, in a sealed package which prevents evaporation of the water from the aqueous dispersion. In use, a part of the composite material or all the composite material can be taken from the package and used for the intended medical purpose. The composite material according to the invention is suitable for making rigid or flexible dressings, for immobilizing and fixing limbs and for making supporting dressings and supporting structures in the case of muscular weakness and joint injuries. It is also suitable for making orthopedic structures which are applied for correcting deformations.

Furthermore, the composite material according to the invention can be used as a repair material for already existing supporting dressings and orthopedic structures, for example for repairs to prostheses.

In all the abovementioned applications, the composite material can also be layered in several superposed plies.

For producing the composite material according to the invention, aqueous polymer dispersions can in principle be used, such as are formed by means of conventional emulsion polymerization processes. Some of the examples given below are for such conventional polymerization processes.

PREPARATION EXAMPLE 1

6 g of a copolymer of acrylamide and N-tert-butylacrylamide in 1:1 weight ratio, dissolved in 180 ml of water, as a protective colloid and 12 g of a 10% solution of an acidic phosphoric acid ester of a fatty alcohol-/ethylene oxide adduct as an emulsifier and 0.69.g of sodium laurylsulfate were placed into a flask provided with stirrer, reflux condenser, thermometer and gas inlet tube. Under a nitrogen atmosphere, 30 g of vinyl acetate and then 80% of an aqueous solution of 0.9 g of potassium persulfate and a solution of 0.06 g of sodium sulfite in water were added. The reaction mixture was heated slowly to 75° C. and, after the polymerization had started, a solution of 0.48 g of sodium bicarbonate was added. The batch was sized such that 289 ml of water in total were used. Within the next two hours, a further 261 g of vinyl acetate were added. After the polymerization was substantially complete, the remainder of the potassium persulfate solution was added and the polymerization batch was heated at 90° C. until visible reflux ceased. The dispersion was allowed to cool to 25° C., with slow stirring.

A readily flowing, homogeneous dispersion having a viscosity of 900 cP (according to Epprecht) and a K value of 59 was obtained.

PREPARATION EXAMPLE 2

Example 1 was repeated, but with the difference that a higher-molecular copolymer of acrylamide and N-tert.-butylacrylamide (K value 104) was used. A readily flowing and spreadable dispersion was obtained, which had a K value of 64.6 and a viscosity of 2,100 cP (Epprecht). In this dispersion again, no settling was observed on storage for more than 1 year.

PREPARATION EXAMPLE 3

In the manner described in the preceding examples, the copolymerization of 279 g of vinyl acetate and 9.6 g of crotonic acid was carried out, using 284 cm³ of water in total. However, the following quantities of protective colloid and emulsifier were used:

- 6.0 g of acrylamide/N-tert.-butylacrylamide copolymer (K value 98, 1:1 weight ratio);
- 18.0 g of a 10% solution of the phosphated ethylene oxide addition products to coconut fatty alcohol;
- 1.4 g of lauryl sulfate.

A homogeneous dispersion was obtained which showed excellent flow behavior and was soluble in dilute alkalis. The viscosity was 1,500 cP (Epprecht) and the K value was 61.

The dispersion was stored for more than 1 year without a detrimental change being observed.

PREPARATION EXAMPLE 4

Example 3 was repeated, but with the difference that 9 g of acrylamide/N-tert.-butylacrylamide copolymer were now used in place of 6 g thereof.

A readily spreadable, alkali-soluble dispersion having a viscosity of 3,400 cP (Epprecht) was obtained, which was still unchanged after storage for more than 1 year.

PREPARATION EXAMPLE 5

A copolymer of 2-ethylhexyl acrylate, methyl methacrylate and a small proportion of methacrylic acid was prepared in the following way.

- 195.64 parts by weight of deionized water
- 3.50 parts by weight of $C_{12}/C_{14}$-fatty alcohol ethersulfate (degree of ethoxylation 4); 100% of active substance
- 0.24 part by weight of potassium peroxodisulfate
- 0.5 part by weight of sodium hydrogen carbonate were placed into a reactor. The latter was flushed with nitrogen for 20 minutes and then heated to 75° C. Separately therefrom, the following emulsion was prepared in a stock vessel:

- 246.9 parts by weight of deionized water 1.5 parts by weight of $C_{12}/C_{14}$-fatty alcohol ethersulfate (degree of ethoxylation 4)
5.00 parts by weight of nonionic emulsifier
1.9 parts by weight of peroxodisulfate
225.4 parts by weight of 2-ethylhexyl acrylate
254.8 parts by weight of methyl methacrylate
9.8 parts by weight of methacrylic acid.

A solution of 0.24 part by weight of potassium peroxodisulfate and 9.56 parts by weight of deionized water was prepared in a dropping funnel.

Feeding of the pre-emulsion into the reaction vessel was started at a temperature of 75° C., and the emulsion was added within about 2 hours by maintaining the exothermic reaction. The internal reaction temperature was 78° to 82° C. The solution of 0.24 part by weight of potassium peroxodisulfate in 4.56 parts by weight of deionized water, prepared in the dropping funnel, was then added for re-initiation. For this purpose, the reaction mixture was held for 60 minutes at temperatures between 85° and 90° C. After cooling to 30° C., the mixture was neutralized with a solution of 5 parts by weight of sodium hydrogen carbonate in 45 parts by weight of deionized water.

The copolymer was obtained in the form of an aqueous dispersion.

PREPARATION EXAMPLE 6

The vinyl acetate dispersion according to the invention was prepared as follows:

3 kg of a commercially available aqueous dispersion of vinyl acetate homopolymer with polyvinyl alcohol as the protective colloid and a solids content of 65% by weight is first introduced into a beaker. With fast stirring, 750 g of commercially available homopolyvinyl acetate redispersion powder were slowly added. The powder was here added in stages, that is to say the addition was interrupted several times, the stirrer was turned off and the system was given an opportunity for "degassing", that is to say allowing air which had been stirred in to escape again. After complete addition of the powder, the dispersion, which can be used according to the invention, had a solids content of 72% by weight.

In the application examples which follow, composite materials according to the invention were prepared by impregnating various carrier materials with the aqueous polyvinyl acetate dispersion obtained according to Preparation Example 6. The coated or impregnated carrier materials were then squeezed by passing them through a nip located between two rollers rotating in opposite directions and wound up to a roll.

The rolls thus produced were packaged in sealable polyethylene bags.

APPLICATION EXAMPLE 1

A knitted glass fiber fabric of 7.5 cm width and a weight per unit area of 300 g/m² was treated in the manner described above. The impregnating agent applied was 300 g/m².

APPLICATION EXAMPLE 2

A knitted polyester/cotton fabric of 1 cm width and a weight per unit area of 95 g/m² was treated as described above. The impregnating agent applied was 250 g/m².

APPLICATION EXAMPLE 3

Test cylinders were wound in such a way that the individual plies are arranged congruently and flush one above the other. The internal diameter of the test cylinders was 75 mm in each case. To determine the stability, the wound test cylinders are dried for 24 hours at 50° C. and 30% relative humidity and then stored for one hour at room temperature (20° C.).

In this way, the following test cylinders were wound and dried.

APPLICATION EXAMPLE 4

Four-ply test cylinder from application Example 1.

APPLICATION EXAMPLE 5

8-Ply and 12-ply test cylinders from Application Example 2 were wound.

TESTING

The stability of the test cylinders, wound and conditioned according to application example 3, from application examples 4 and 5 is determined by means of a universal testing machine (Franck).

The test cylinders are placed between a pair of pressure plates in such a way that the axis of the test cylinder is arranged parallel to the pressure plates. The testing force was determined which is required for deforming the test cylinder by 1 cm (testing speed 50 mm/minute).

| Application Example | Number of plies in test cylinder | Width of the test cylinders | Force for 1 cm deformation |
| --- | --- | --- | --- |
| 4 | 4 | 7.5 cm | 228 N |
| 5 | 8 | 11 cm | 130 N |
| 5 | 12 | 11 cm | 310 N |

The above test results show that the supporting dressings according to the invention have excellent strength after drying.

We claim:

1. A composite material for making a rigid supporting dressing for medical use, said composite material enclosed in a water tight package, and comprising a porous flexible carrier impregnated with an aqueous dispersion containing from 30% to 80% of a film forming polymer the polymer particles of which are capable of film formation on said flexible carrier thereby forming a rigid supporting dressing on removal of water.

2. Composite material according to claim 1, characterized in that the porous carrier is in the form of an absorbent filament-shaped material.

3. Composite material according to claim 1 characterized in that the porous carrier is a foam material.

4. A composite material according to claim 1 characterized in that the aqueous polymer dispersion is the dispersion of a homopolymer or copolymer based on a vinyl derivative.

5. A composite material according to claim 4, characterized in that a homopolymer or copolymer of vinyl acetate is present as the polymer in the polymer dispersion.

* * * * *